(12) United States Patent
Kim

(10) Patent No.: US 7,993,584 B1
(45) Date of Patent: Aug. 9, 2011

(54) CAUSTIC, CORROSIVE OR CONDUCTIVE LIQUID/GAS SENSOR USING LATERAL-FIELD-EXCITED RESONATOR

(75) Inventor: Yoonkee Kim, Freehold, NJ (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 103 days.

(21) Appl. No.: 12/313,791

(22) Filed: Nov. 21, 2008

Related U.S. Application Data

(63) Continuation-in-part of application No. 10/863,831, filed on Jun. 1, 2004, now abandoned.

(51) Int. Cl.
  *G01N 33/00* (2006.01)
  *C12Q 1/68* (2006.01)
(52) U.S. Cl. .......................... 422/68.1; 422/50
(58) Field of Classification Search .................. 422/50, 422/68.1
See application file for complete search history.

(56) References Cited

U.S. PATENT DOCUMENTS

| | | | |
|---|---|---|---|
| 6,463,787 B1 * | 10/2002 | Schumacher et al. | 73/24.06 |
| 6,544,478 B1 | 4/2003 | Oyama et al. | |
| 7,075,216 B1 * | 7/2006 | Vetelino | 310/338 |
| 7,335,336 B1 | 2/2008 | Kim | |

OTHER PUBLICATIONS

Hu, Y., et al, Laboratory for Surface Science & Technology, Orono, ME "A Lateral Field Excited Liquid Acoustic Wave Sensor", IEEE Conference Records-Abstracts, International Symposium, Honolulu, HI, pp. 12&13 (2003).

* cited by examiner

*Primary Examiner* — Lore Jarrett
(74) *Attorney, Agent, or Firm* — Michael Zelenska; Stephen J. Harbulak

(57) ABSTRACT

A sensor for sensing a property of an analyte includes a QCM resonator that has a crystal substrate that includes an electrode depositing surface and an analyte contact surface that are physically separated. The resonator further includes a plurality of electrodes operatively connected with the electrode depositing surface and laterally spaced apart one from another.

17 Claims, 2 Drawing Sheets

(TFE)

(LFE)

CAUSTIC, CORROSIVE OR CONDUCTIVE LIQUID/GAS SENSOR USING LATERAL-FIELD-EXCITED RESONATOR

CONTINUATION-IN-PART

This application is a Continuation-In-Part of U.S. Patent And Trademark Office application Ser. No. 10/863,831, entitled, "Corrosive or Conductive Liquid/Gas Sensor Using Lateral-Field-Excited Resonator," which was filed on Jun. 1, 2004 now abandoned, by the same inventor herein. This Continuation-In-Part is being filed under 35 USC §120 and 37 CFR §1.53, and priority from that application is hereby claimed.

GOVERNMENT INTEREST

The invention described herein may be manufactured, used, imported, sold, and licensed by or for the Government of the United States of America without the payment of any royalty thereon or therefor.

FIELD OF THE INVENTION

The present invention relates generally to acoustic sensors and, more particularly, to sensors comprising quartz crystal microbalance resonators.

BACKGROUND OF THE INVENTION

Sensors comprising quartz crystal microbalance (QCM) resonators are generally known. QCM resonators may function as acoustic wave resonators to provide highly sensitive detection mechanism for fluid analytes. As illustrated in FIG. 1, a typical QCM resonator is shown generally at 100 and comprises a piezoelectric crystal substrate 102 located between a pair of electrodes 104 having leads 106. In this configuration, an electric field may be generated by the electrodes 104 and extend therebetween along a transverse axis, or through the thickness, of the piezoelectric crystal substrate 102. Hence in this configuration the QCM resonator may be termed a thickness field excitation (TFE) resonator. The electrodes 104 and the crystal 102 are dimensioned to achieve an optimal resonance condition.

One particular example of a TFE resonator is described in U.S. Pat. No. 6,544,478 to Oyama et al wherein the resonator is arranged in a multi-channel structure. The resonator includes a crystal substrate that has four mutually opposed electrodes disposed on opposite sides of the substrate. In operation, the TFE resonator may be used to detect and quantitatively analyze components of a sample from a variation in fundamental resonant frequency and impedance when a surface of one of the pair of electrodes is immersed into either a sample gas or solution.

While the above TFE resonators have been suitable for use with non-caustic analytes, it has been found that when these resonators are immersed into a caustic substance the electrodes tend to deteriorate as a result of contact between the electrodes and a caustic, corrosive, or electrode-degrading analyte, which oftentimes causes electrode deterioration, reduced sensitivity, and inaccurate sensor readings. When QCM electrodes are made with a gold layer on top of a chrome or titanium adhesion layer on the surface of quartz, corrosive analytes such as a strong acid will attack the adhesion layer when contacting the electrode. For example, aqua regia, which is a mixture of nitric acid and hydrochloric acid, will even dissolve gold, resulting in lifting the prior art electrode off of the adhesion layer. Also, use of these resonators is restricted to non-conductive analytes because of the possibility that the electric field may become shorted. Accordingly, to date, no suitable QCM resonator is available for analyzing a caustic, corrosive, or conductive analyte. Thus, there has been a long-felt need for resonators configured with electrodes that are not damaged or deteriorated because of contact with caustic, corrosive, or conductive analytes.

SUMMARY OF THE INVENTION

In order to satisfy the long-felt need for resonators configured with electrodes that are not damaged or deteriorated because of contact with caustic, corrosive or conductive analytes and in accordance with the present invention, a sensor for sensing a property of an analyte is provided in several embodiments with a resonator that comprises a crystal substrate that has an electrode depositing surface and an analyte contact surface that are physically separated. The resonator further comprises a plurality of electrodes operatively connected with the electrode depositing surface and laterally spaced apart one from another. In accordance with this invention, no electrodes contact a caustic, corrosive, or conductive analyte, and only the bare quartz side contacts the analyte, while prior art devices with electrodes on both sides will have at least one electrode contacting such analyte causing electrode deterioration, reduced sensitivity, and inaccurate sensor readings. This invention's sensors are configured for testing caustic, corrosive, or conductive analytes with the electrode depositing surface and electrodes physically separated from an analyte contact surface.

In one embodiment of the present invention depicted in FIG. 2, a sensor for sensing a property of an analyte comprises a resonator 10 that comprises a crystal substrate that has an electrode depositing surface and an analyte contact surface. A plurality of electrodes may be operatively connected with the electrode depositing surface and laterally spaced apart one from another. The sensor may further comprise a housing for supporting the resonator and the analyte and that comprises a base and an analyte support container to function as an analyte contact surface. The analyte support container may comprise an aperture wherein the resonator is located such that the electrode depositing surface is disposed proximate the aperture of the analyte support container, but still physically separated therefrom. It is also noted that in sensor configurations for testing a conductive analyte, the physical separation of the electrode depositing surface from the analyte contact surface prevents the alternating electric field from leaking into the analyte, which avoids the loss of acoustic energy that is usually caused by such leakage and allows improved sensitivity.

BRIEF DESCRIPTION OF THE DRAWINGS

The following detailed description is made with reference to the accompanying drawings, in which.

DETAILED DESCRIPTION OF THE DRAWINGS

One embodiment of the present invention concerns a quartz crystal microbalance (QCM) resonator that is suitable for use with a caustic, corrosive, or conductive analyte. In other embodiments of the present invention, sensor devices employing a QCM resonator suitable for use with a conductive or corrosive analyte are presented. All embodiments of this invention require a lateral field excitation (LFE) QCM resonator that propagates a bulk acoustic wave (BAW).

Figure 1:
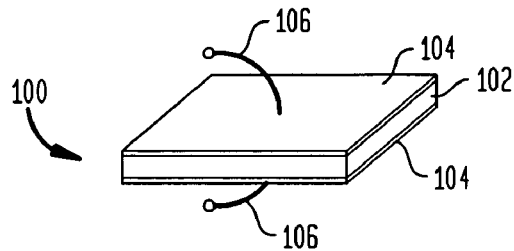
FIG. 1 is a perspective view of a prior art QCM resonator.
Figure 2:
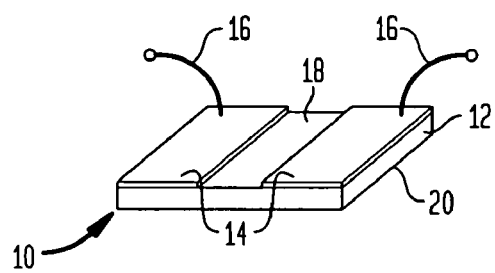
FIG. 2 is a perspective view of a QCM resonator in accordance with an embodiment of the present invention.

Referring now to FIG. 2, a QCM resonator in accordance with one embodiment of the present invention is illustrated generally at 10. In this embodiment, the QCM resonator 10 comprises a substrate 12, electrodes 14 and electrode leads 16. The substrate 12 may comprise a piezoelectric crystal material such as quartz that functions in such a way that when the quartz is contacted with a property of an analyte to be measured, it varies in resonant frequency and impedance in a known manner. Examples of properties of an analyte to be measured include viscosity and density. The substrate 12 may comprise any suitable outer geometrical configuration such as square or circular and comprises an electrode depositing surface 18 and an analyte contact surface 20 that are physically separated so that the analyte is confined to the analyte contact surface 20 and cannot contact the electrode depositing surface 18. Although not illustrated as such, the analyte contact surface 20 may be coated with a material such as an antibody and/or a polymer that may enhance sensitivity or selectivity of the QCM resonator 10.

In accordance with a feature of this embodiment of the present invention, the electrodes 14 are located away from any contact with an analyte that is limited and confined to the analyte contact surface 20. As illustrated, both of the electrodes are located on the electrode depositing surface 18, although, other locations on the substrate may be possible so long as the electrode depositing surface 18 is physically separated from the analyte contact surface 20. The electrodes 14 may comprise any suitable, highly conductive, metallic substance, although gold is preferred, and may be applied to the substrate 12 via photolithography or deposited via, e.g., evaporation, sputtering, or electroplating. Electrode leads 16 may be connected at one end to the electrodes 14 and at the other to a suitable AC source at the resonant frequency of the resonator 10 and measuring device (not shown).

In this configuration, an electric field may be generated by the electrodes 16 along a lateral axis of the piezoelectric crystal substrate 12, thus the QCM resonator is termed an LFE QCM resonator. As in the TFE case, the electrodes 16 and the crystal 12 may be dimensioned to achieve an optimal resonance condition.

Another embodiment, in accordance with the present invention, is illustrated in FIG'S 3 and 4 wherein a sensor device 50 comprises a QCM resonator 52 and a housing 54 for an analyte 56. The QCM resonator 52 may be similar to the QCM resonator 10 described above and similarly comprises a substrate 58 including an electrode depositing surface 60, electrodes 62 deposited to the electrode depositing surface 60 and electrode leads 64, with the electrode depositing surface 60 and electrode leads 64 physically separated from the analyte support container 66 functioning as an analyte contact surface.

The housing 54 may comprise an analyte support container 66 and a base 68. The analyte support container 66 and the base 68 may each comprise a moldable polymeric material such as a polyethylene or a polyamide and may also each comprise generally cylindrical outer configurations, as illustrated. The analyte support container 66 is illustrated as having a generally closed configuration including a chamber 69 for the analyte 56 and an aperture 70, although, it will be understood that the analyte support container 66 may comprise a lid or cover (not shown) or be connected to a pipe or conduit (also not shown) for communication of the analyte to the chamber in a continuous flow-like process.

Figure 3:
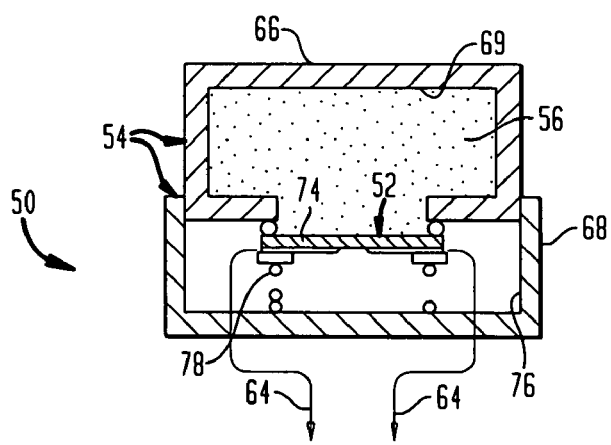
FIG. 3 is a cross section of a sensor device including a QCM resonator in accordance with another embodiment of the present invention.
Figure 4:
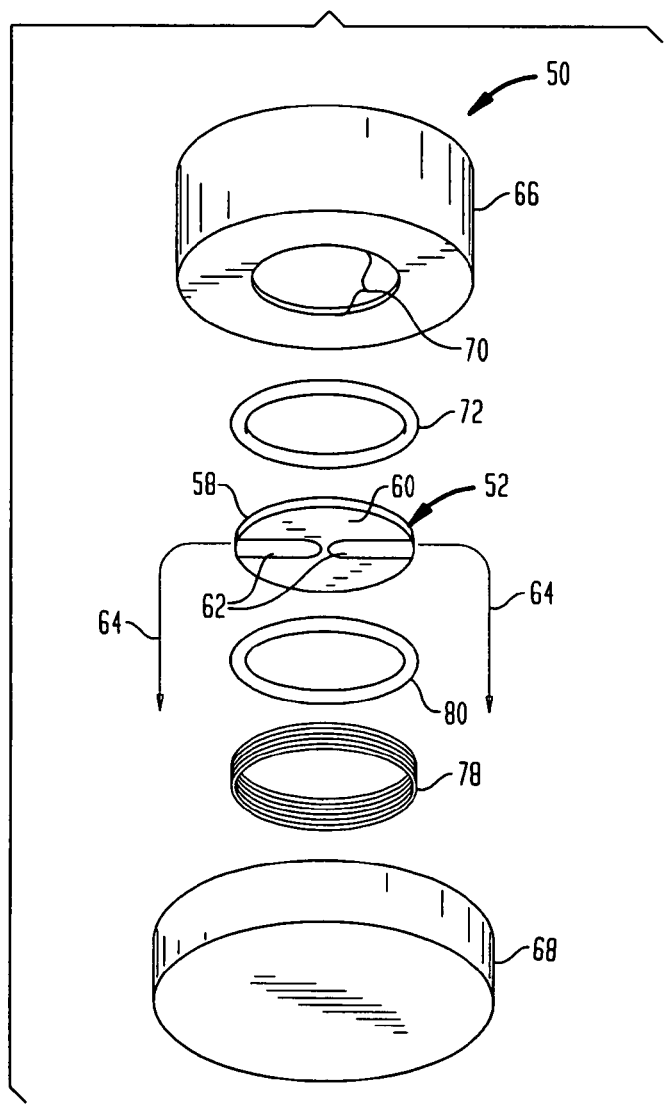
FIG. 4 is an exploded view of the sensor device of FIG. 3.

The base 68 comprises an open end (not numbered) that is preferably dimensioned to receive the analyte support container 66, which is best seen in FIG. 3. A seal, such as an O-ring 72, is provided to seal the analyte 56 adjacent an analyte support surface 74 from a cavity 76 of the base 68. A spring 78 may be interposed between the base 68 and the QCM resonator 52 for biasing the resonator adjacent the O-ring 72, which is, in turn, biased adjacent the analyte support container 66. An insulating ring 80 may be employed to insulate the spring 78 and prevent shorting the electrodes 62. This embodiment allows for an easy replacement of the QCM resonator 52 when the need of the replacement of the QCM resonator 52 arises. For example, when the resonator 52 is damaged or when use of the resonator 52 with a different coating (not shown) for sensing different analyte is necessary.

Thus, this invention provides three sensor embodiments for sensing the properties of electrode-degrading, corroding or conductive analytes, to include caustic analytes, where the electrode depositing surface is physically separated from the analyte contact surface so that the analyte is confined to the analyte contact surface or analyte support container and the electrodes will not contact the analyte.

While the present invention has been described in connection with what are presently considered to be the most practical and preferred embodiments, it is to be understood that the present invention is not limited to these herein disclosed embodiments. Rather, the present invention is intended to cover all of the various modifications and equivalent arrangements included within the spirit and scope of the appended claims.

What I claim is:

1. A sensor for sensing properties of an electrode-degrading analyte, comprising:
    a lateral field excitation quartz crystal microbalance (QCM) resonator having a crystal substrate, wherein the QCM resonator is supported by a housing;
    the crystal substrate of the QCM resonator comprises an analyte contact surface on a first side and an electrode depositing surface on a second side;
    said housing having a base and an analyte support container;
    a plurality of electrodes connected to said electrode depositing surface and are laterally spaced apart from another, wherein the electrodes are only connected to the electrode depositing surface;
    said QCM resonator propagates a bulk acoustic wave and generates an electric field;
    said analyte contact surface of said crystal substrate is on the opposite side of the electrode depositing surface and said electrodes, and confines said electrode-degrading analyte to said analyte contact surface without contacting said electrode depositing surface and said electrodes in order to test said electrode-degrading analyte without damaging said electrodes and said sensor; and a seal interposed between said QCM resonator and said analyte support container.

2. The sensor for sensing properties of the electrode-degrading analyte, as recited in claim 1, further comprising a spring located between said base and said QCM resonator.

3. The sensor for sensing the properties of the electrode-degrading analyte, as recited in claim 2, further comprising an insulating ring interposed between said spring and said QCM resonator.

4. The sensor for sensing the properties of the electrode-degrading analyte, as recited in claim 3, further comprising said analyte support container and said base each having a cylindrical outer configuration.

5. The sensor for sensing the properties of the electrode-degrading analyte, as recited in claim 1, wherein said crystal substrate comprises a piezoelectric crystal.

6. The sensor for sensing the properties of the electrode-degrading analyte, as recited in claim 1, further comprising said electrode-degrading analyte being a caustic analyte.

7. A sensor for sensing the properties of a conductive analyte, comprising: a lateral field excitation quartz crystal microbalance (QCM) resonator having a crystal substrate, and
   propagates a bulk acoustic wave and generates an electric field;
   the crystal substrate of the QCM resonator comprises an analyte contact surface on one side and an electrode depositing surface on an opposite side;
   a plurality of electrodes connected to said electrode depositing surface, and are laterally spaced apart from another, wherein the electrodes are only connected to the electrode depositing surface;
   a housing supports said QCM resonator and said conductive analyte;
   said housing having a base and an analyte support container with an aperture to harmlessly contact and confine said conductive analyte;
   said analyte support container is positioned on the opposite side of the electrode depositing surface and said electrodes, and restricts said conductive analyte to said analyte support container;
   said QCM resonator being positioned to permit said analyte contact surface to be disposed proximate said aperture; and
   said analyte support container being configured to test said conductive analyte without short circuiting said electrodes and said sensor.

8. The sensor for sensing the properties of the conductive analyte, as recited in claim 7, further comprising a seal interposed between said QCM resonator and said analyte support container.

9. The sensor for sensing the properties of the conductive analyte, as recited in claim 8, further comprising a spring located between said base and said QCM resonator.

10. The sensor for sensing the properties of the conductive analyte, as recited in claim 9, further comprising said analyte support container and said base each having a cylindrical outer configuration.

11. The sensor for sensing the properties of the conductive analyte, as recited in claim 7, wherein said crystal substrate comprises a piezoelectric crystal.

12. A sensor for sensing the properties of an electrode-corroding analyte, comprising:
   a lateral field excitation quartz crystal microbalance (QCM) resonator having a crystal substrate;
   said crystal substrate of the QCM resonator comprises an analyte contact surface on a first side and an electrode depositing surface on a second side;
   said crystal substrate, having a resonant frequency that varies based on contact with a predetermined property of said electrode-corroding analyte, propagates a bulk acoustic wave and generates an electric field;
   a plurality of electrodes being operatively connected to said electrode depositing surface, and are laterally spaced apart from another, wherein the electrodes are only connected to the electrode depositing surface;
   a housing comprising a base and an analyte support container with an aperture;
   said housing supports said QCM resonator;
   said analyte contact surface of said crystal substrate is on the opposite side of the electrode depositing surface and said electrodes, and confines said electrode-corroding analyte to said analyte contact surface to test said electrode-corroding analyte without degrading performance of said electrodes and said sensor; and
   a seal interposed between said QCM resonator and said analyte support container.

13. The sensor for sensing the properties of the electrode-corroding analyte, as recited in claim 12, further comprising a spring located between said base and said QCM resonator.

14. The sensor for sensing properties of the electrode-corroding analyte, as recited in claim 13, wherein the seal comprises an o-ring.

15. The sensor for sensing the properties of the electrode-corroding analyte, as recited in claim 14, further comprising said analyte contact surface and said base each having a cylindrical outer configuration.

16. The sensor for sensing the properties of the electrode-corroding analyte, as recited in claim 15, wherein said crystal substrate comprises a piezoelectric crystal.

17. The sensor for sensing the properties of the electrode-corroding analyte, as recited in claim 12, further comprising said electrode-corroding analyte being a caustic analyte.

\* \* \* \* \*